United States Patent
KenKnight et al.

(10) Patent No.: US 8,224,443 B2
(45) Date of Patent: Jul. 17, 2012

(54) METHOD FOR CONTROLLING PACEMAKER THERAPY

(75) Inventors: Bruce KenKnight, Maple Grove, MN (US); Steven D. Girouard, Chagrin Falls, OH (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 1439 days.

(21) Appl. No.: 11/745,823

(22) Filed: May 8, 2007

(65) Prior Publication Data
US 2008/0281371 A1 Nov. 13, 2008

(51) Int. Cl.
*A61N 1/362* (2006.01)
(52) U.S. Cl. .......................................... 607/9
(58) Field of Classification Search .................. 607/9
See application file for complete search history.

(56) References Cited

U.S. PATENT DOCUMENTS

| | | |
|---|---|---|
| 5,103,821 A | 4/1992 | King |
| 5,240,009 A | 8/1993 | Williams |
| 5,273,049 A | 12/1993 | Steinhaus et al. |
| 5,280,792 A | 1/1994 | Leong et al. |
| 5,400,795 A | 3/1995 | Murphy et al. |
| 5,645,070 A | 7/1997 | Turcott |
| 5,682,900 A | 11/1997 | Arand et al. |
| 5,779,645 A | 7/1998 | Olson et al. |
| 5,817,133 A | 10/1998 | Houben |
| 5,819,741 A | 10/1998 | Karlsson et al. |
| 5,857,977 A | 1/1999 | Caswell et al. |
| 5,944,743 A | 8/1999 | Janssens |
| 6,223,078 B1 | 4/2001 | Marcovecchio |
| 6,266,554 B1 | 7/2001 | Hsu et al. |
| 6,275,732 B1 | 8/2001 | Hsu et al. |
| 6,285,907 B1 * | 9/2001 | Kramer et al. .................. 607/9 |

(Continued)

FOREIGN PATENT DOCUMENTS

| WO | WO 2007/014134 A2 | 2/2007 |
|---|---|---|
| WO | WO 2008/043099 A2 | 4/2008 |

OTHER PUBLICATIONS

Bucchi et al., "Wild-Type and Mutant HCN Channels in a Tandem Biological-Electronic Cardiac Pacemaker," *Circulation*, 114(10): 992-999 (2006).

(Continued)

*Primary Examiner* — Carl H Layno
*Assistant Examiner* — Jeremiah Kimball
(74) *Attorney, Agent, or Firm* — Finnegan, Henderson, Farabow, Garrett & Dunner, LLP

(57) ABSTRACT

The present invention includes a method for controlling pacemaker therapy in a patient with an implanted biological pacemaker. The method may include pacing a heart at a predetermined rate using an electronic pacemaker and configuring the pacemaker to periodically enter a biological pacemaker weaning mode. The weaning mode may include ceasing pacing for at least a predetermined length of time and monitoring the heart to detect electrical depolarizations of a ventricle of the heart during the predetermined length of time. The weaning mode may further include determining the length of time between the cessation of pacing and the detected electrical depolarization and determining if the length of time between the cessation of pacing and the detected electrical depolarization is less than a maximum predetermined interval. The pacemaker therapy may be withheld as long as the length of time is less than the maximum predetermined interval. Further, if the length of time exceeds a maximum interval, the pacemaker will exit the weaning mode.

20 Claims, 6 Drawing Sheets

U.S. PATENT DOCUMENTS

| | | | |
|---|---|---|---|
| 6,308,095 B1 | 10/2001 | Hsu et al. | |
| 6,312,388 B1 | 11/2001 | Marcovecchio et al. | |
| 6,434,417 B1 | 8/2002 | Lovett | |
| 6,449,503 B1 | 9/2002 | Hsu | |
| 6,650,937 B2 | 11/2003 | Kerver | |
| 6,671,558 B1 | 12/2003 | Soykan et al. | |
| 6,775,574 B1 | 8/2004 | Soykan et al. | |
| 6,923,784 B2* | 8/2005 | Stein | 604/67 |
| 6,959,212 B2 | 10/2005 | Hsu et al. | |
| 2002/0019593 A1* | 2/2002 | Hsu et al. | 600/513 |
| 2003/0149457 A1* | 8/2003 | Tcheng et al. | 607/48 |
| 2004/0137621 A1 | 7/2004 | Rosen et al. | |
| 2004/0215251 A1* | 10/2004 | Sharma et al. | 607/9 |
| 2004/0254134 A1 | 12/2004 | Marban et al. | |
| 2005/0002914 A1 | 1/2005 | Rosen et al. | |
| 2005/0021089 A1 | 1/2005 | Sharma | |
| 2005/0043766 A1 | 2/2005 | Soykan et al. | |
| 2005/0192637 A1 | 9/2005 | Girouard et al. | |
| 2005/0288721 A1 | 12/2005 | Girouard et al. | |
| 2006/0009812 A1 | 1/2006 | Daum et al. | |
| 2006/0015146 A1 | 1/2006 | Girouard et al. | |
| 2006/0074455 A1* | 4/2006 | Strandberg | 607/30 |
| 2006/0212080 A1 | 9/2006 | Hartley et al. | |
| 2006/0271118 A1* | 11/2006 | Libbus et al. | 607/9 |
| 2008/0103536 A1* | 5/2008 | Xiao | 607/3 |
| 2008/0103537 A1* | 5/2008 | Sigg et al. | 607/3 |

OTHER PUBLICATIONS

Cohen et al., "The Why, What, How and When of Biological Pacemakers," *Nature Clinical Practice*, 2(8): 374-375 (2005).

Gepstein, "Stem Cells as Biological Heart Pacemakers," *Expert Opin. Biol. Ther.* 5(12): 1531-1537 (2005).

Kehat et al., "Electromechanical Integration of Cardiomyocytes Derived from Human Embryonic Stem Cells," *Nature Biotechnology*, 22(10): 1282-1289 (2004).

Plotnikov et al., "Biological Pacemaker Implanted in Canine Left Bundle Branch Provides Ventricular Escape Rhythms That Have Physiologically Acceptable Rates," *Circulation*, 109(4): 506-512 (2004).

Plotnikov et al., "Tandem Biological/Electronic Pacing Increases Versatility over Electronic Pacing Alone While Maintaining Safety," Heart Rhythm Society 27th Annual Scientific Sessions, Abstracts (2006).

Potapova et al., "Human Mesenchymal Stem Cells as a Gene Delivery System to Create Cardiac Pacemakers," *Circulation Research*, 94(7): 952-959 (2004).

Rosen et al., "Genes, Stem Cells and Biological Pacemakers," *Cardiovascular Research*, 64: 12-23 (2004).

Rosen, "Biological Pacemaking: In Our Lifetime?" *Heart Rhythm* 2(4): 418-428 (2005).

Qu et al., "Expression and Function of a Biological Pacemaker in Canine Heart," *Circulation*, 107(8): 1106-1109 (2003).

International Search Report for International Application No. PCT/US2008/058265 mailed Aug. 25, 2008.

Written Opinion of the International Searching Authority for International Application No. PCT/US2008/058265 mailed Aug. 25, 2008.

\* cited by examiner

METHOD FOR CONTROLLING PACEMAKER THERAPY

FIELD OF THE INVENTION

The present invention pertains generally to methods and systems for phasing in a biological pacemaker. The methods and systems can provide a transition from an electronic pacemaker to a biological pacemaker. Additionally, cardiac rhythm management may be provided by the concurrent use of an implantable pulse generator (IPG) pacemaker and a biologic pacemaker.

BACKGROUND OF THE INVENTION

The heart is a muscular organ that pumps blood throughout the body. In a normal, healthy heart the pumping is initiated by periodic electrical depolarizations that originate in the sinoatrial node. The electrical depolarizations spread throughout the myocardium, causing the heart to contract, and forcing blood into the aorta and pulmonary artery.

In healthy hearts, the myocardial depolarization occurs in a coordinated sequence, which facilitates adequate pumping. As noted, the initial depolarization generally originates in the sinoatrial node and spreads throughout the atria, thereby causing the atria to contract, forcing blood into the ventricles. Subsequently, the depolarization passes through the atrioventricular node and, through a group of specialized conducting myocardial fibers (Purkinje fibers), is transmitted through the interventricular septum and ventricles. The right and left ventricles are thus depolarized and contract to pump blood through the pulmonary artery and aorta to the body.

Heart disease is a major health problem. Numerous environmental, behavioral, genetic, and/or congenital conditions can lead to chronic or acute damage to the heart. Acute myocardial events, such as a myocardial infarction, may damage portions of the heart's native pacemakers (i.e. sinoatrial and atrioventricular nodes) or conduction systems, and may decrease the overall pumping effectiveness of the heart. Likewise, chronic conditions, such as high blood pressure, valvular disease, certain types of bacterial or viral infection, and diabetes, may produce slowly-progressing, but similarly damaging effects on the heart.

One way to treat damaged heart muscle cells is to provide pharmaceutical therapies in an effort to restore heart function. Many pharmacologic treatments are effective at improving patient quality of life by increasing cardiac output, preventing arrhythmias, and/or treating symptoms associated with heart failure. However, for some patients, pharmaceutical therapy may be ineffective or inadequate. For example, many patients who have suffered acute or chronic damage to the heart's pacemakers or conduction systems have lasting and/or recurring arrhythmias. Often these arrhythmias result in a loss of chronotropic competence, and consequently these patients are unable to modulate their intrinsic heart rate in response to changing metabolic demands. In addition, in some patients, conduction through the ventricles may be abnormal or intermittent and/or the depolarizations may be asynchronous, whereby contractions of the atria and ventricles are poorly coordinated. Further, many patients have difficulties complying with pharmaceutical regimens. All these conditions may have a deleterious effect on cardiac output, may contribute to the progression of cardiac disease, and may ultimately lead to death.

For many patients, implantable cardiac rhythm management systems (e.g. pacemakers, cardiac resynchronization pacemakers and/or defibrillators) are necessary. Pacemakers generally include a housing (can) that encloses various electrical components, such as a battery, control hardware, communications systems, and/or other diagnostic components. The pacemaker also includes a number of leads and electrodes, which interface with portions of the heart to be stimulated or regions of the heart where physiological signals are sensed. Numerous different pacemakers and/or defibrillators are available, and the specific type of device is selected based on a variety of clinical factors that are evaluated by a physician.

More recently, there has been growing interest in developing pacemakers using cellular sources, which may be implanted or injected into certain regions of the heart to produce a new, biological pacemaker. The cells may be engineered to have electrical properties that mimic natural cardiac pacemakers, but may be implanted at a variety of cardiac locations and may be selected based on particular patient needs. However, the use of biological pacemakers may present some limitations, and even with a biological pacemaker, many patients may still benefit from an implantable device. For example, the biological pacemaker may have inherent limits on cardiac rates that it can achieve, and an implantable device may be needed when higher metabolic demands are encountered. Further, a biological pacemaker may be temporarily or permanently affected by medications or any condition that may affect normal myocardial cells (e.g. infarction). In addition, an implantable device may be desired to monitor, record, and/or transmit information related to patient status, including biological pacemaker status, to healthcare professionals to facilitate continued treatment.

For some biological pacemaker system designs, the biological pacemaker may not begin to provide appropriate rhythm and rate control until some time after implantation. During this time, an implantable electrical pacemaker may be used. However, as the biological pacemaker begins to function and take over the intrinsic pacemaking activity of the heart, it would be useful to determine if sensed cardiac depolarizations originate in the implantable electrical pacemaker, in the biological pacemaker, in an ectopic cardiac site, or in the native pacemaker. In addition, it may be necessary to slowly phase in the biologic pacemaker therapy. This may be desirable when a newly implanted biologic pacemaker has yet to establish reliability, to prevent an abrupt change in demands on the heart due to a rapid change in pacing rate, to facilitate formation of necessary electrical connections between native cardiac tissue and an implanted biologic pacemaker, and/or to provide a back-up pacing should a new biological pacemaker fail to adequately pace the heart.

SUMMARY OF THE INVENTION

One aspect of the present invention includes a method for controlling pacemaker therapy in a patient with an implanted biological pacemaker. The method may include pacing a heart at a predetermined rate using an electronic pacemaker and configuring the pacemaker to periodically enter a biological pacemaker weaning mode. The weaning mode may include ceasing pacing for at least a predetermined length of time and monitoring the heart to detect electrical depolarizations of a ventricle of the heart during the predetermined length of time. The weaning mode may further include determining the length of time between the cessation of pacing and the detected electrical depolarization and determining if the length of time between the cessation of pacing and the detected electrical depolarization is less than a maximum predetermined interval. The pacemaker therapy may be withheld as long as the length of time is less than the maximum predetermined interval. Further, if the length of time exceeds a maximum interval, the pacemaker will exit the weaning mode.

Another aspect of the present invention includes a method for controlling pacemaker therapy in a patient with an implanted biological pacemaker. The method may include pacing a heart at a predetermined rate using an electronic pacemaker and ceasing pacing for at least a predetermined length of time. The heart may be monitored to detect electrical depolarizations of the heart during the predetermined length of time, and the electrical depolarizations of the heart may be evaluated to determine if they originated in an implanted biological pacemaker site. The length of time between the cessation of pacing and the detected electrical depolarization may be determined, and if the time is less than a maximum predetermined interval and if the electrical depolarization originated in the implanted biological pacemaker site, pacing therapy may be withheld.

Another aspect of the present invention includes a method for controlling pacemaker therapy in a patient with an implanted biological pacemaker. The method may include pacing a heart at a predetermined rate using an electronic pacemaker, assessing a time of day or physiologic state of a patient, and ceasing pacing for at least a predetermined length of time if the patient's physiologic state matches a desired predetermined state or the time of day is appropriate. The method may further include monitoring the heart to detect electrical depolarizations of the heart during the predetermined length of time, determining if the length of time between the cessation of pacing and the detected electrical depolarization is less than a maximum predetermined interval, and continuing to withhold pacemaker therapy if the electrical depolarization originated in the implanted biological pacemaker site and the length of time is less than the maximum predetermined interval.

Another aspect of the present invention includes a pacemaker system for use in patients with an implanted biological pacemaker. The pacemaker system may include a pulse generator configured to generate electrical energy for stimulating a heart, at least one electrode configured to provide electrical stimulation to a heart and in electrical communication with the pulse generator, and at least one sensor configured to detect electrical depolarizations of a ventricle of the heart. The system may further include a pacemaker processor configured to control pacing therapy according to at least one predetermined pacing mode and to enter a biological pacemaker weaning mode periodically, wherein the pacemaker is configured to cease pacing therapy for a predetermined length of time, to receive a signal from the at least one sensor indicating a depolarization of a ventricle of the heart after cessation of pacing, to determine the length of time between the cessation of pacing and the detected electrical depolarization, to determine if the length of time between the cessation of pacing and the detected electrical depolarization is less than a maximum predetermined interval, to continue to withhold pacemaker therapy as long as the length of time is less than the maximum predetermined interval, and to exit the pacemaker weaning mode if the length of time is greater than a maximum predetermined interval.

Additional objects and advantages of the invention will be set forth in part in the description which follows, and in part will be obvious from the description, or may be learned by practice of the invention. The objects and advantages of the invention will be realized and attained by means of the elements and combinations particularly pointed out in the appended claims.

DETAILED DESCRIPTION OF THE INVENTION

Figure 1:
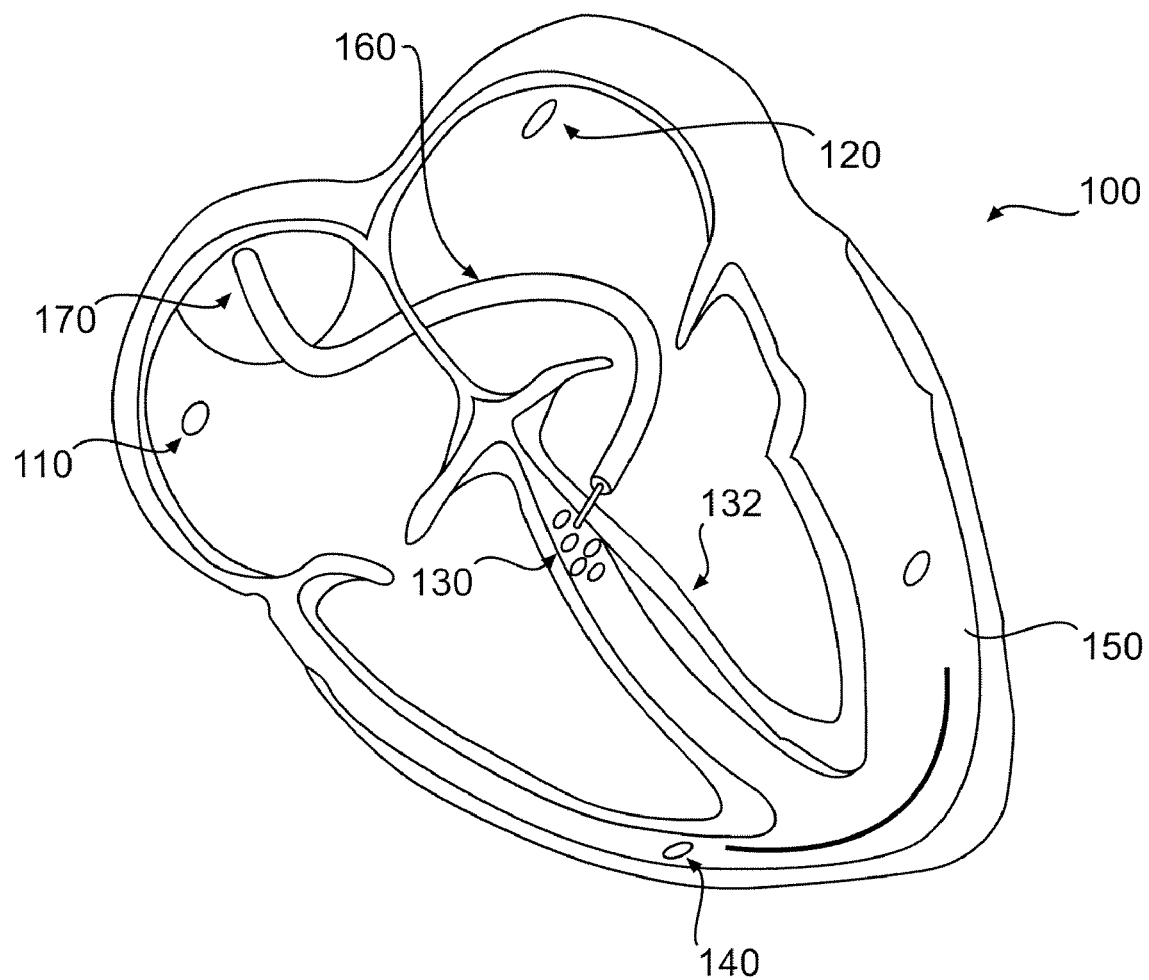
FIG. 1 illustrates a heart including implanted biological pacemakers, according to an exemplary disclosed embodiment.

Detailed description of exemplary embodiments of the present invention will now be made with reference to the accompanying drawings. Wherever possible, the same reference numbers will be used throughout the drawings to refer to the same or like parts. It is to be understood that both the foregoing general description and the following detailed description are exemplary and explanatory only and are not restrictive of the invention, as claimed.

In the following detailed description, reference is made to the accompanying drawings which form a part hereof and in which is shown by way of illustration specific embodiments in which the invention may be practiced. These embodiments are described in sufficient detail to enable those skilled in the art to practice and use the invention, and it is to be understood that other embodiments may be utilized and that electrical, logical, and structural changes may be made without departing from the spirit and scope of the present invention. The following detailed description is, therefore, not to be taken in a limiting sense and the scope of the present invention is defined by the appended claims and their equivalents. Throughout the description the term 'biological pacemaker' will be understood to refer to a pacemaker comprising living cells that are implanted, injected, or otherwise placed into the body for electrical stimulation of cardiac tissue. In addition, biological pacemakers can include native cells or tissues that are altered (e.g. by gene therapy) to produce pacemaker activity. Further, the terms 'pacemaker,' 'implantable device,' 'implantable pacemaker,' 'pacemaker/defibrillator', 'cardioverter', 'cardiac resynchronization pacemaker', and 'pacemaker/ICD' will be understood to refer to a pacemaker, defibrillator, pacemaker/defibrillator combination, or any other implantable device having electrical circuits and conductive leads and electrodes comprising non-living materials capable of stimulating the heart. It should also be noted that the examples and cardiac complexes presented here are representative, and are not actual cardiac complexes recorded from patients.

The present disclosure pertains to devices and methods for assessing the function of an implanted biological pacemaker, and to devices and methods for providing pacing therapy using an electronic pacemaker to a patient having an implanted biological pacemaker. In some embodiments, the devices and methods of the present disclosure may be used to transition a patient from an electronic pacemaker to a biological pacemaker.

After implantation, an implantable biological pacemaker may not begin to function immediately. For example, it may take several days, or even longer, for implanted biological pacemakers to express genes to the extent required to produce sufficient levels of proteins needed to form cell-to-cell electrical connections and/or ion channel proteins responsible for spontaneous depolarizations. Further, for an initial period of time newly-implanted cells may not be able to withstand rigorous metabolic demands, and/or may not produce sufficiently regular rhythms with adequate rates to support sufficient cardiac output. The devices and methods of the present disclosure can be used to allow gradual transitions from heart rate and rhythm controlled by an electronic pacemaker to heart rate and rhythm controlled by a biological pacemaker. The gradual transition may facilitate formation of appropriate cell-to-cell connections, appropriate expression and membrane localization of ion channel proteins, allow implanted tissue to adapt to new metabolic demands, and/or allow a physician to assess the performance of a biological pacemaker during a transition period.

The devices and methods of the present disclosure include a conventional pacemaker for providing primary pacing therapy. Periodically, the conventional pacemaker may enter a pacemaker weaning mode wherein the pacemaker will cease pacing for a certain length of time, and if a biological pacemaker is functioning properly, allow the biological pacemaker to provide the primary heart pacemaker control for some time before switching back to the electronic pacemaker therapy. In some embodiments, the electronic pacemaker may cease pacing at predetermined time intervals. In other embodiments, the electronic pacemaker may cease pacing when a patient is in a desired physiologic state such as resting or sleeping.

Conventional implantable pacemakers/defibrillators require a pulse generator comprising a battery and electrical circuits configured to stimulate cardiac sites to effect depolarization and contraction. Unlike conventional pacemakers, biological pacemakers are comprised of living cells or tissue that may be implanted or otherwise implanted in or around the heart. The cells or tissue may be selected and/or produced to provide periodic electric stimulation, much like the pacemaker cells of the heart's sinoatrial or atrioventricular nodes. Various aspects of biological pacemakers are described in Rosen et al, "Genes, stem cells, and biological pacemaker," Cardiovascular Research vol. 64: 12-23 (2004); Gepstein, Lior, "Stem cells as biological pacemakers," Expert Opin. Biol. Ther. vol. 5(12): 1531-1536 (2005); and U.S. Patent Publication 2004/0254134 to Marban et al., all of which are hereby incorporated by reference in their entirety.

Biological pacemakers may be produced from a variety of suitable cellular or tissue sources. For example, biological pacemakers may be produced from pluripotent cell lines, which may be treated and/or genetically altered to produce desired electrical properties. Suitable cell lines may include, but are not limited to, peripheral blood stem cells, bone-marrow derived stem cells, cardiac myoblasts, skeletal myoblasts, embryonic stem cells, cord-blood derived stem cells, adult mesenchymal stem cells, or any other cellular source that may be treated, conditioned, or engineered to produce periodic electrical depolarizations. Further, suitable cell or tissue sources may include autologous, allogeneic, or xenogeneic sources. Any suitable cellular source may be selected.

As noted, the cells or tissue used for the biological pacemaker may be selected, treated, conditioned, or genetically engineered to produce desired properties. For example, the cells or tissues may be selected or engineered to express certain genes that will provide desired electrical properties. Such genes may include various ion channels selected to produce periodic electric depolarizations and repolarizations. Other genes may be selected to facilitate formation of gap junctions between cells or tissue to be used as a biological pacemaker and the surrounding myocardium. Further, genes may be selected to provide desired responses to metabolic changes, neural or hormonal changes, or to pharmaceuticals. In addition, genes may be selected to enhance cell viability or enhance engraftment after implantation.

Cells or tissue selected for the biological pacemakers may be treated prior to or after implantation to enhance their function or encourage differentiation into cardiomyocytes or cardiomyocyte-like cells having desired electrical properties. For example, selected stem cells may be pre-treated ex-vivo to encourage differentiation into cardiomyocytes or to stimulate formation of gap junctions. Further, prior to implantation, selected cells or tissue may be mixed with other materials that may facilitate implantation or enhance engraftment or viability. For example, the cells or tissue may be mixed with selected culture media, extracellular matrix materials, pharmaceuticals, agents selected to control gene expression, antibiotics, and/or any other suitable material.

In addition, some biological pacemakers may be created by genetically altering regions of native cardiac tissue. For example, myocardial cells may be transfected with genes encoding various ion channel proteins that will facilitate spontaneous electrical depolarizations. For example, such genes and delivery methods are described in Plotnikov et al., "Biological Pacemaker Implanted in Canine Left Bundle Branch Provides Ventricular Escape Rhythms That Have Physiologically Acceptable Rate," Circulation vol 109: r31-r37 (2004), which is herein incorporated by reference in its entirety. It should be understood that treatment of existing myocardium by these methods is also meant to describe a method of implanting a biological pacemaker.

Selected biological pacemakers may be implanted at a number of suitable cardiac locations. The specific location may be selected based on patient-specific clinical factors that are assessed by a physician. Further, some patients may have biological pacemakers implanted at more than one location. FIG. 1 illustrates a heart 100 with biological pacemakers illustrated at several different locations. It should be understood that the illustrated biological pacemakers of FIG. 1 are provided to indicate where the pacemakers may be implanted, but the location and number of biological pacemakers may vary. For example, some patients may have only one biological pacemaker, but other patients may have several.

As shown, biological pacemakers may be implanted within the interventricular septum, within the atria, or at various locations within the right ventricle or left ventricle. For some patients, a right atrial biological pacemaker 110 may be selected to mimic pacing from the SA node. In other patients a left atrial biological pacemaker 120 may be selected with or without a right atrial biological pacemaker 110. In other patients, an interventricular septum biological pacemaker 130 may be selected. For such patients, the pacemaker may be implanted at any location within the septum 132, including for example, near the AV node or more inferiorly near the apex. Further, a right ventricular biological pacemaker 140 or left ventricular biological pacemaker 150 may be used, and any suitable ventricular location may be selected. As noted previously, some patients may have more than one biological pacemaker, including combinations of atrial, ventricular, or septal pacemakers.

Suitable biological pacemakers may be implanted using a variety of techniques. For example, a catheter 160 may be passed into the heart through the superior vena cava 170 or inferior vena cava (not shown), and the catheter 160 may be advanced to the desired implantation site. As shown in FIG. 1, to implant an interventricular biological pacemaker 130 or left ventricular biological pacemaker 150, the catheter 160 may be passed through the interatrial septum, and the pacemaker cells or tissue may be injected at the selected location using a needle or other instrument. Further, the biological pacemaker may be implanted during the implantation procedure for an implantable conventional pacemaker and/or ICD. In some embodiments, the implantable pacemaker may be implanted, and optionally function conventionally, prior to implantation of the biological pacemaker. After implantation of the implantable pacemaker, template waveforms representing cardiac depolarizations originating at the site of the biological pacemaker may be produced by stimulating the myocardium at the location of the biological pacemaker (e.g. using a stimulating lead on the catheter 160). Further, the implantable pacemaker may be used to sense and store signals representative of the template waveforms, and perform other monitoring or support functions as necessary.

Figure 2:
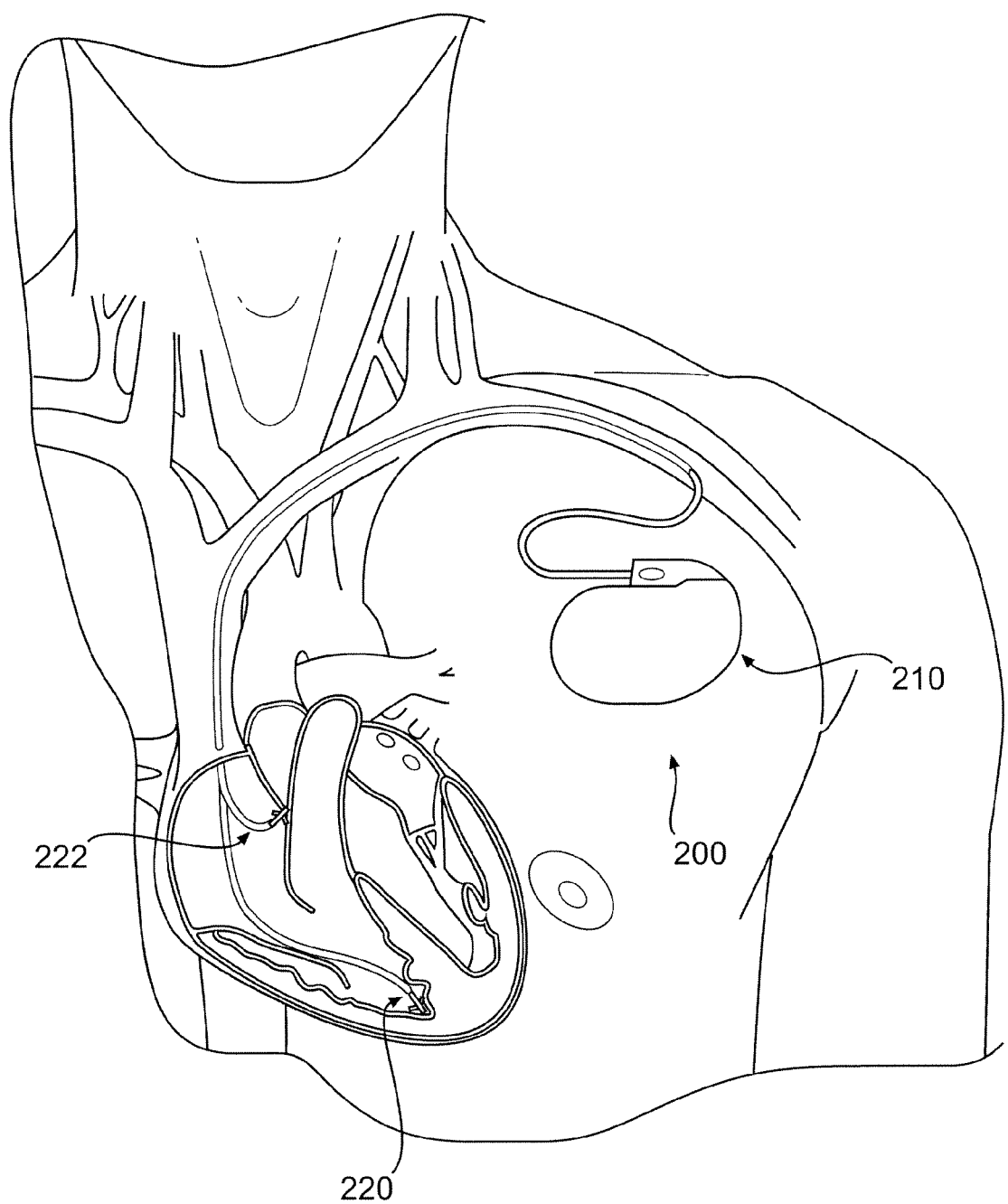
FIG. 2 illustrates a pacemaker implanted in a patient, according to an exemplary disclosed embodiment.

FIG. 2 illustrates an exemplary embodiment of a pacemaker 200 that may be implanted in conjunction with a biological pacemaker. As shown, the pacemaker 200 includes a pulse generator (can) 210 implanted in a subclavian site. Two right heart leads 220, 222 are connected to the pulse generator 210 and fed into the heart through the superior vena cava. First lead 220 is configured to stimulate the right ventricle, and second lead 222 is configured to stimulate the right atrium.

It should be noted that a variety of different lead configurations may be selected. For example, as shown two right-heart leads 220, 222 are provided. However, any suitable number of leads may be selected. For example, one or more left heart leads may be provided through one or more coronary veins. In addition, any suitable lead types may be selected, including, for example, epicardial leads, subcutaneous leads, and/or intravascular leads. In addition, suitable leads may include physical connections with a power source, or wireless leads may be selected. Further, the leads may include sensing and/or stimulating electrodes, may include unipolar leads, bipolar leads or any other lead polarity, may include defibrillation electrodes and/or patch electrodes, and may include any other desired sensors, including for example, pressure, chemical, or gas sensors. Any suitable lead and/or electrode design may be selected.

The pacemaker 200 may be configured to provide any pacing or defibrillation therapy as is known in the art. For example, any desired pacing mode (e.g. VDD, AAI, DDDR) or therapy (e.g. cardiac resynch therapy, post-MI therapies, and/or angiogenic stimulation) may be selected based on patient-specific characteristics. The pacemaker 200 may be configured to provide pacing therapy immediately following implantation of the biological pacemaker until the biological pacemaker has become engrafted and functions properly. In other embodiments, the pacemaker 200 may be configured to continuously or periodically evaluate the performance of one or more biological pacemakers and to provide pacing therapy if the biological pacemaker is determined to be functioning improperly. Further, as noted previously, the pacemaker 200 may also include an ICD configured to provide cardioversion or defibrillation shocks if needed.

Figure 3:
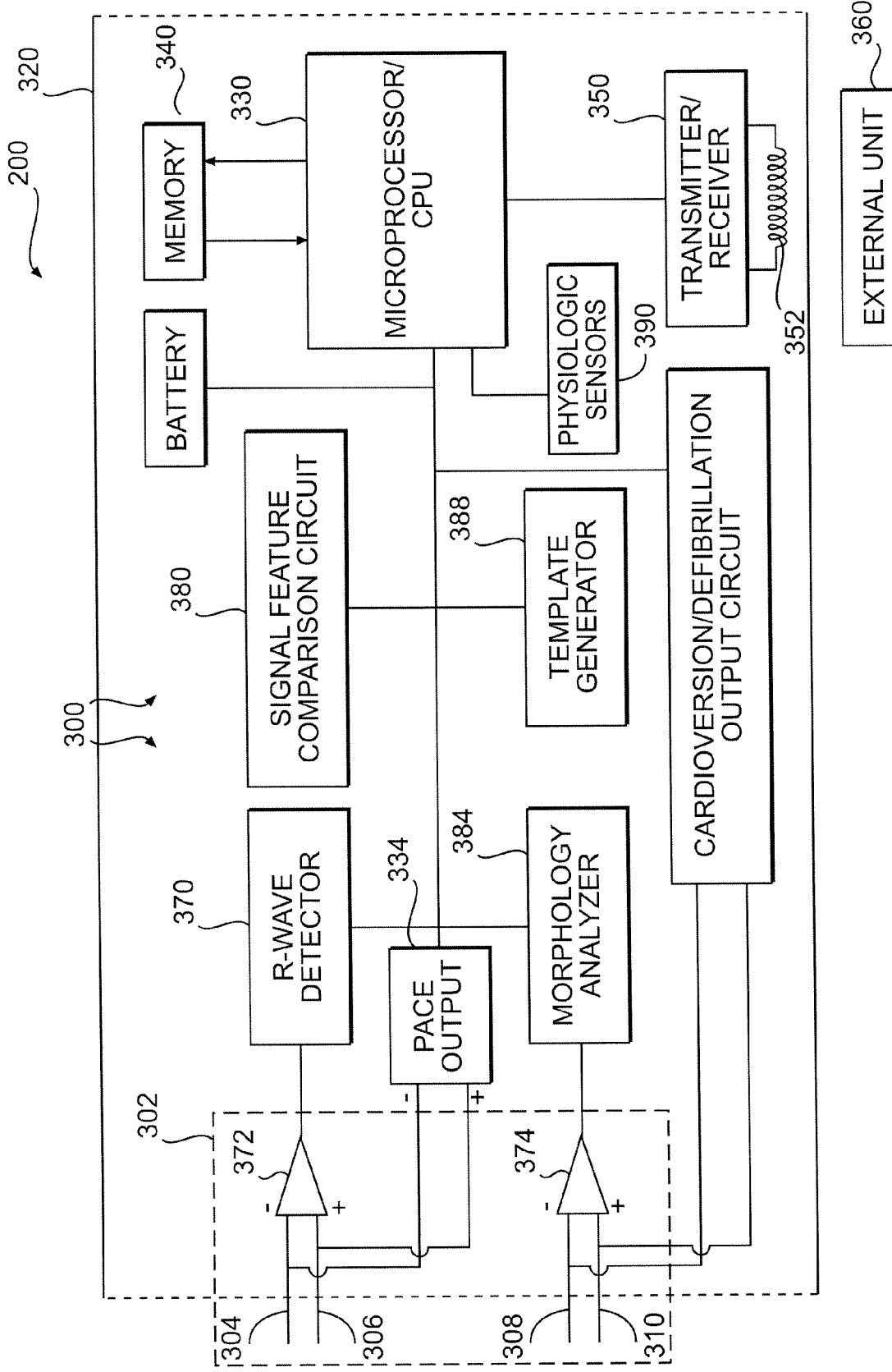
FIG. 3 illustrates a block diagram of the components of the pacemaker of FIG. 2.

Referring now to FIG. 3, there is shown a block diagram of one embodiment of pacemaker 200. The pacemaker 200 includes control system circuitry 300 for receiving cardiac signals from a heart and delivering electrical energy to the heart. The control system circuitry 300 includes a sensing system 302 attached to at least one catheter (e.g. leads). The sensing system 302 includes terminals 304, 306, 308, 310 for connection to electrodes attached to the surface of the leads. In one embodiment, the pacing leads 220, 222 are electrically connected to at least one of terminals 304, 306, 308, 310 and to the control system circuitry 300 through an electrically insulated conductor provided within the elongate body of the leads 220, 222.

In one embodiment, the control system circuitry 300 of the pacemaker 200 is encased and hermetically sealed in a housing 320 suitable for implanting in a human body as is known in the art. A connector block (not shown) is additionally attached to the housing 320 of the pacemaker 200 to allow for the physical and the electrical attachment of the leads 220, 222 to the pacemaker and the encased control system circuitry 300.

In one embodiment, the control system circuitry 300 of the pacemaker 200 is a programmable microprocessor-based system, with a microprocessor 330 and a memory circuit 340 which contains parameters for various pacing, defibrillation, and sensing modes, and stores data indicative of cardiac signals received by the control system circuitry 300. A transmitter/receiver circuit 350 is additionally coupled to the control system circuitry 300 and the memory circuit 340 to allow the pacemaker 200 to communicate with and receive programming instructions and transmit data to and from an external unit 360, as is known in the art. The transmitter circuit 350 may include any suitable wireless communication system. For example, the transmitter circuit 350 and the external unit 360 can use a wire loop antenna 352 and a radio frequency or inductive coupling telemetric link to receive and transmit signals and data to and from the external unit 360 and the control system circuitry 300. In this manner, programming commands or instructions are transferred to the microprocessor 330 of the pacemaker 200 after implantation, and stored cardiac data pertaining to sensed electrical activity or therapies applied to the heart are transferred to the external unit 360.

The pacemaker 200 may be configured to detect, measure, and/or record cardiac electrical signals. For example, leads 220, 222 may include one or more electrodes configured to facilitate near-field or far-field sensing, as is known in the art. Further, the sealed housing 320 of the pacemaker may serve as an electrode for stimulation and/or sensing. Additionally, other leads and electrodes may be positioned at suitable locations within the heart, or at other intracorporeal or extracorporeal locations.

The sensing electrodes may be electrically connected to a sense amplifier 372, 374, and the output of at least one sense amplifier 372 is connected to an R-wave detector 370. The R-wave detector 370 serves to sense and amplify cardiac signals, including cardiac complexes sensed from the heart, and to apply signals indicative thereof to a signal feature comparison circuit 380. The signal feature comparison circuit 380 is coupled to the microprocessor 330. Among other things, microprocessor 330 responds to signals from the R-wave detector 370 by providing pacing signals to a pace output circuit 334, according to the programmed pacing mode. In one embodiment, the pace output circuit 334 provides output pacing signals to terminals 304 and 306, which connect to the pacing electrodes of leads 220, 222.

In some embodiments, at least one pair of electrodes may be configured for far-field sensing. Further, sensed far-field signals may be connected with a second sense amplifier 374 that passes an amplified signal to a morphology analyzer circuit 384. The morphology analyzer circuit 384 receives and processes the cardiac complexes detected within the cardiac signals. In one embodiment, the morphology analyzer circuit 384 receives cardiac signals, including cardiac complexes representative of the cardiac cycle from the sensing system. Cardiac complexes analyzed by the morphology analyzer circuit 384 can include detected P-waves, QRS-complexes, and R-waves. In one embodiment, the morphology analyzer circuit 384 includes an analog filter for filtering cardiac signal noise sensed by the electrodes. In an exemplary embodiment, the cardiac signals are then band limited before arriving at an analog-to-digital filter which converts the analog signals into digital signals suitable for processing. In an alternative embodiment, the cardiac signals are filtered through an analog peak detector to extract the maximum and minimum cardiac signal values for each sensed cardiac complex.

In processing sensed cardiac complexes, the morphology analyzer circuit 384 windows a cardiac complex sensed in two or more cardiac signals. In one embodiment, the morphology analyzer circuit 384 locates and extracts information from one or more predetermined features of sensed cardiac complexes. The type of information extracted by the morphology analyzer circuit 384 can include the time of occurrence of one or more predetermined features and the amplitude values of the one or more predetermined features. In one embodiment, the predetermined features include regions of cardiac complexes that are repeatably identifiable in subsequent cardiac complexes. For example, such features may include a maximum deflection of the cardiac complex, a beginning of a cardiac complex as indicated by a predetermined deviation of the cardiac signal from a baseline signal, and an ending of a cardiac complex as indicated by a return of the first cardiac signal to a baseline signal. In one embodiment, the features are selectively programmed into the medical device system.

A template generator circuit 388 is coupled to the sensing system 302. The template generator circuit 388 receives information from the morphology analyzer 384. In one embodiment, the information received from the morphology analyzer 384 includes the information extracted from cardiac signals by the morphology analyzer circuit 384. In one embodiment, the template generator circuit 388 may create a numerical representation of sensed cardiac complexes using the extracted information.

In some embodiments, the information provided by morphology analyzer circuit 384 and/or template analyzer circuit 388 may be used to determine if sensed cardiac depolarizations originate in an implanted biological pacemaker, or in another cardiac location. A variety of methods may be used to determine the origin of sensed cardiac depolarizations, including for example, comparison of vectors derived from sensed cardiac beats with one or more template vectors, comparison of cardiac intervals measured using combinations of near-field and far field sensors, and/or morphology analysis. Suitable methods for determining if a sensed cardiac depolarization originates in an implanted biological pacemaker are described in commonly-assigned U.S. patent application Ser. No. 11/745,667, herein incorporated be reference in its entirety.

The pacemaker 200 may further include one or more physiologic sensors 390. Such sensors can include any type of sensor that will provide information useful for determining whether or not it is appropriate to cease pacing therapy by pacemaker 200 to allow an implanted biological pacemaker to pace the heart. For example, during an early period after implantation, or any time when there may be concern about the ability of the biological pacemaker to provide adequate pacing function, it may be desirable to provide primary pacing therapy using the pacemaker 200 and to allow the biological pacemaker to pace only during periods of lower stress and/or metabolic demands. Accordingly, in some embodiments, sensors 390 may include any type of sensor configured to provide information related to metabolic demands and/or cardiac output. Further, in some embodiments, sensors 390 may be configured to provide information related to whether or not a patient is sleeping. Suitable rest or sleep sensors may include, for example, temperature sensors, heart rate sensors, activity sensors, sensors configured to determine if a patient is lying down (e.g. posture sensors/incline sensors), and/or any other suitable sensor type as is known in the art.

Figure 4:
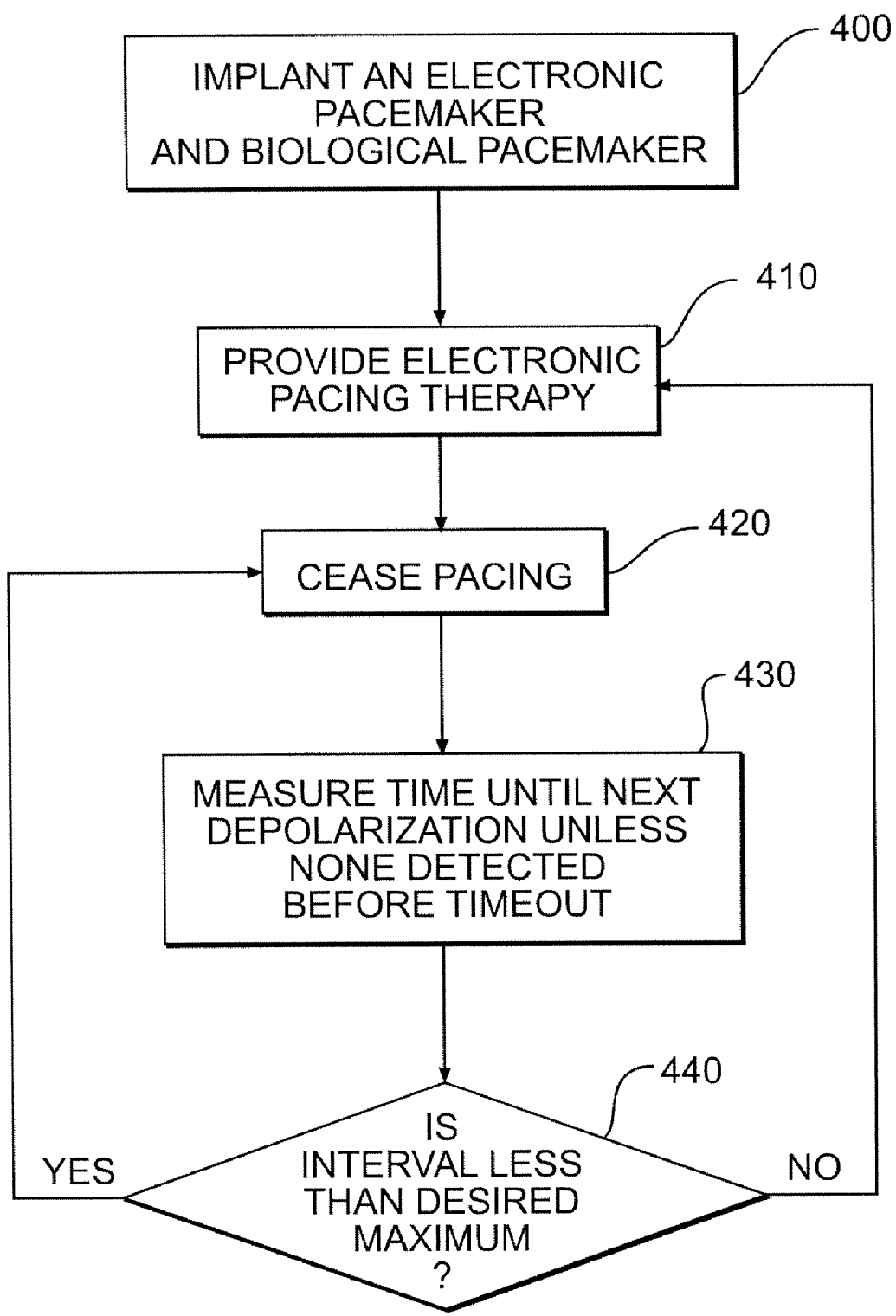
FIG. 4 illustrates a method for controlling pacemaker therapy in a patient with an implanted biological pacemaker, according to an exemplary disclosed embodiment.

FIG. 4 illustrates a method for controlling pacemaker therapy in a patient with an implanted biological pacemaker, according to an exemplary disclosed embodiment. According to the method of the present disclosure, an electronic pacemaker and biological pacemaker are first implanted, as indicated at Step 400. Any suitable electronic and/or biological pacemaker may be selected, as described above. The initial primary pacing therapy will be provided by the electronic pacemaker, as indicated at 410.

The primary pacing therapy, as provided by the electronic pacemaker, can include any suitable pacing therapy selected by a healthcare provider. For example, a physician may program or select the specific pacemaker design, lead and electrode placement, and/or pacing mode based on a patient's clinical condition and physician preference.

After some time has elapsed, the electronic pacemaker will cease pacing for at least a predetermined length of time, as indicated at step 420. While the pacing therapy is being withheld by the electronic pacemaker, the electronic pacemaker will continue to monitor the heart to detect depolarizations of the ventricles, with such depolarizations being expected to originate in a biological pacemaker. Next, the pacemaker will determine the time between the last paced beat and sensed depolarizations, as indicated at step 430. If the interval between the last paced beat is less than a predetermined maximum value, the pacemaker will continue to withhold pacing therapy 440. Subsequently, the pacemaker will continue to evaluate the interval between depolarizations, and if the interval meets certain criteria, as described in detail below, the pacemaker will continue to withhold pacing therapy.

Generally, the pacemaker will withhold pacing therapy as long as the biological pacemaker provides pacing at a suitable rate. The rate may vary based on patient-specific characteristics, and/or metabolic demand. Generally, acceptable rates may be between about 60 beats per minute (bpm) or about 100 bpm (i.e. having about a 1 second to about a 0.6 second interval between ventricular contractions). However, for some patients slower or faster rates may be acceptable.

As noted, the pacemaker may evaluate the interval between successive ventricular depolarizations in the absence of electronic pacing to determine if electronic pacing therapy should be withheld. It should be noted that in patients with competent SA or AV nodes and/or ectopic pacing sites, depolarizations may occur spontaneously before the biological pacemaker depolarizes. In some embodiments, the electronic pacemaker will determine that any ventricular depolarization is acceptable as long as certain rate, rhythm, and/or morphology constraints are met, as described further below. In other embodiments, the electronic pacemaker will evaluate the sensed ventricular depolarization to determine if the depolarization likely originated in the biological pacemaker. The electronic pacemaker may further take into consideration the site of origin of the depolarization in determining whether or not to resume pacing therapy.

Referring again to Step 420, the pacemaker microprocessor 330 may control cessation of pacing therapy based on a number of different factors. For example, in some embodiments, pacing therapy will be withheld at predetermined time intervals. In some embodiments, the time intervals may be selected as regular intervals. For example, after an implantation of the biological pacemaker, the electronic pacemaker may provide primary pacing therapy for several days or weeks, or as indicated by a physician. Subsequently, electronic pacing may be stopped for at least a predetermined interval, and as long the biological pacemaker is providing adequate pacing, the electronic pacemaker may continue to withhold pacing. The electronic pacemaker may continue to withhold pacing as long as the biological pacemaker is functioning properly or for a selected time (e.g. 1 to several hours).

In some embodiments, the amount of time that the biological pacemaker is allowed to assume the primary pacing function may be increased as the biological pacemaker function improves and/or as the time since implantation increases. For example, shortly after implantation, the biological pacemaker may assume the primary pacing function for a short time (e.g. thirty minutes to one hour) each day. This time may be increased as the function of the biological pacemaker improves and/or as time progresses. For example, the time that the biological pacemaker functions each day may be increased by steady increments, or as dictated by a physician. Alternatively, the biological pacemaker may assume the primary pacing function at set time intervals (e.g. for a few minutes each hour, every several hours, twice a day, only during sleep, etc).

Figure 5:
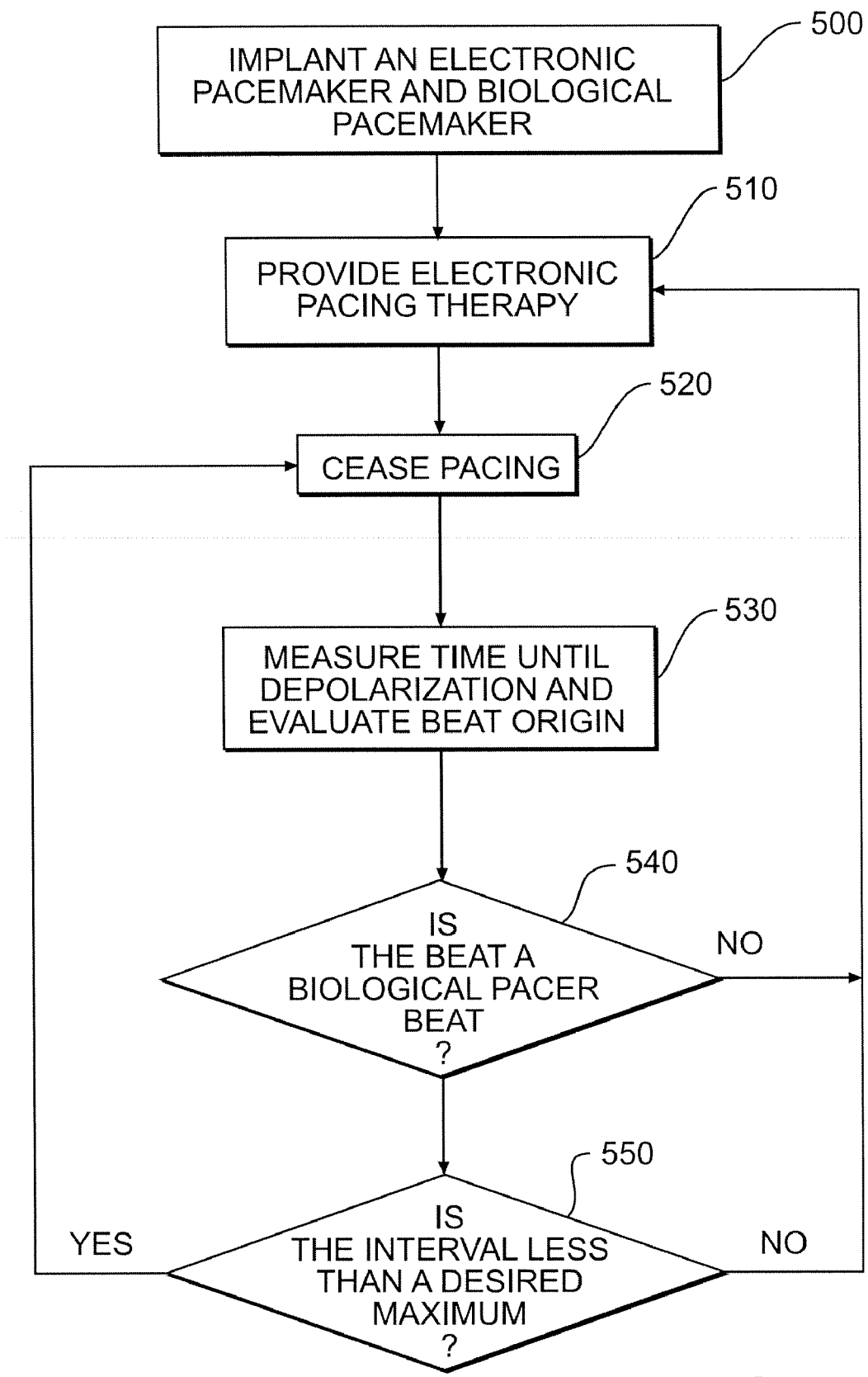
FIG. 5 illustrates a method for controlling pacemaker therapy in a patient with an implanted biological pacemaker, according to an exemplary disclosed embodiment.

FIG. 5 illustrates a method for controlling pacemaker therapy in a patient with an implanted biological pacemaker, according to an exemplary disclosed embodiment. Again, according to the method of the present disclosure, an electronic pacemaker and biological pacemaker are first implanted, as indicated at Step 500, and the initial primary pacing therapy will be provided by the electronic pacemaker, as indicated at 510.

After some time has elapsed, the electronic pacemaker will cease pacing for at least a predetermined length of time, as indicated at step 520. While the pacing therapy is being withheld by the electronic pacemaker, the electronic pacemaker will continue to monitor the heart to detect depolarizations of the ventricles. Next, the pacemaker will determine the time between the last paced beat and sensed depolarizations, as indicated at step 530. In addition, in some embodiments, the pacemaker may monitor various features of cardiac complexes to determine if a paced beat originates in a biological pacemaker or another cardiac location (e.g. the SA node, AV node, or ectopic site), as indicated at Step 540. As noted previously, suitable methods for determining if a sensed cardiac depolarization originates in an implanted biological pacemaker are described in commonly-assigned U.S. patent application Ser. No. 11/745,667, herein incorporated be reference in its entirety.

If the pacemaker determines that the depolarization does not originate in a biological pacemaker, the pacemaker may resume the primary pacing therapy. However, if the cardiac complex does originate in the biological pacemaker, the pacemaker may further evaluate the interval between cessation of pacing and cardiac depolarization, as indicated at 550. As described previously, if the interval is less than a predetermined maximum, the pacemaker may withhold pacing therapy. Subsequently, the pacemaker will continue to evaluate the interval between depolarizations, and if the interval meets certain criteria, the pacemaker will continue to withhold pacing therapy.

In other embodiments, the pacemaker may be configured to withhold pacing therapy as long as a certain percentage of ventricular depolarizations originate within the biological pacemaker. For example, if 50-100% percent of the ventricular depolarizations originate in a biological pacemaker site, and an acceptable ventricular rate is present, than the pacemaker may withhold primary pacing therapy.

Figure 6:
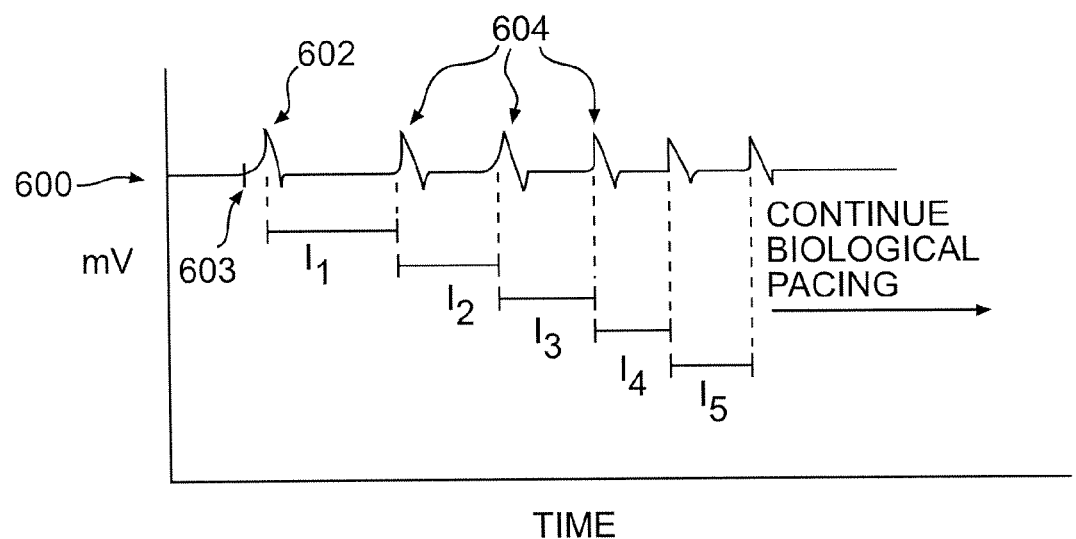
FIG. 6 illustrates electrocardiograms that may be used to control pacemaker therapy in a patient with an implanted biological pacemaker, according to an exemplary disclosed embodiment.
Figure 6:
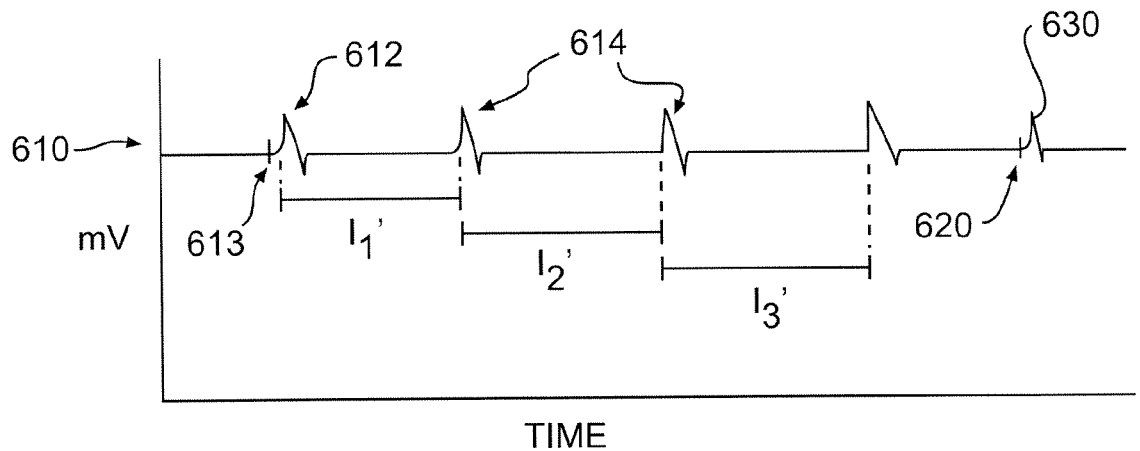

In some embodiments, the biological pacemaker may exhibit a lag time after cessation of pacing before pacing at a suitable rate. Therefore, the electronic pacemaker may be configured to allow a longer beat-to-beat interval for a certain time after cessation of pacing. FIG. 6 illustrates electrocardiograms that may be used to control pacemaker therapy in a patient with an implanted biological pacemaker, according to an exemplary disclosed embodiment. The electrocardiograms are exemplary and do not represent actual patient recordings.

FIG. 6 illustrates a first electrocardiogram 600. Here a pacemaker stimulating pulse 603 produces a depolarization 602. Subsequently, pacing is withheld by the pacemaker, and biological pacemaker induced complexes 604 are seen after intervals I1, I2, I3, I4, I5. As shown, the first interval after cessation of pacing I1 is longer than subsequent intervals I2-I5. Further, the intervals decrease as time passes after cessation of pacing. Therefore, the biological pacemaker exhibits a lag in pacing immediately following cessation of pacing.

To account for this lag, the electronic pacemaker may monitor the intervals after cessation of electronic pacing. Initially, the electronic pacemaker may allow a longer interval (e.g. corresponding to a rate between 30-50 bpm). However, longer intervals may not be acceptable to continue to meet bodily metabolic demands. Therefore, the pacemaker may be configured to shorten the maximum allowable interval as time passes. For example, after cessation of pacing by the electronic pacemaker, the pacemaker may monitor the intervals between biological pacemaker complexes 604. If after a certain time (e.g. 2-10 seconds, 10-30 seconds, 30 seconds to 1 minute), or within a certain number of depolarizations (e.g. less than 10 depolarizations, less than 20 depolarizations), the interval or average interval between two or more depolarizations has not decreased to a desired length acceptable for a given patient's metabolic demands and/or coexisting medical conditions, than the electronic pacemaker may resume pacing.

FIG. 6 illustrates a second electrocardiogram 610 with a pacemaker stimulating pulse 613 and a consequent depolarization 612. Subsequent to pacing pulse 613, pacing by the electronic pacemaker is withheld, and biological pacemaker complexes 614 follow at intervals I1', I2', I3'. In this case, however, the intervals I1', I2', and I3' do not decrease, and the electronic pacemaker therefore determines that the cardiac rate remains too slow for a patient's needs. Therefore, after allowing several biological pacemaker depolarizations 614, and determining that the biological pacemaker has not responded after a sufficient period of time, the electronic pacemaker provides a stimulating pulse 620 to produce a subsequent depolarization 630, and resumes the primary pacing function.

In other embodiments, a patient may be able to control which pacemaker provides the primary pacing function. For example, if, during a period in which the biological pacemaker is providing the primary pacing function, the patient feels ill, dizzy, or otherwise unsatisfied with the pacing therapy, the patient may provide a signal to the electronic pacemaker to order the pacemaker to resume pacing. Such a signal may be effected through a variety of suitable means, including for example, RF telemetry systems, a magnet or any other communication system as is known in the art.

As noted previously, the electronic pacemaker can be configured to communicate with an external monitor 360. The external monitor can include, for example, a recording and transmitting unit to store and/or transmit information related to the patient's health and/or function of the electronic and/or biological pacemaker to a physician. Such information can include any available physiologic data, including, for example, electrocardiograms, rate trends, body temperature, blood gas levels, activity level, cardiac output, rhythm data, and/or any other information that a healthcare provider may wish to interpret to monitor a patient.

In some embodiments, the external unit can include a bedside monitor that a patient would keep at a suitable bedroom location. In one embodiment, the electronic pacemaker may be configured to provide primary pacing therapy. Periodically, the electronic pacemaker may cease pacing to allow the biological pacemaker to function. However, in some embodiments, the electronic pacemaker may be configured to only cease pacing if a patient is lying on a bed or is within a certain distance from the monitoring unit. In this way, the electronic pacemaker will provide the primary pacing function when the patient is not resting or sleeping.

In some embodiments, the electronic pacemaker may provide backup pacing during periods in which the biologic pacemaker provides the primary pacing therapy. For example, the electronic pacemaker may be operated in an inhibited pacing mode (e.g. VVI mode) wherein a sensed ventricular depolarization within the programmed VVI rate interval will cause the electronic pacemaker to withhold pacing. Therefore, as noted previously, the electronic pacemaker may be configured to operate in an inhibited pacing mode, with an escape interval that is longer than an expected biologic pacing interval. The electronic pacemaker will therefore only deliver pacing pulses if the biologic pacemaker rate becomes too slow, or if the biologic pacemaker periodically skips normal beats. Therefore, in some embodiments, cessation of pacing by the electronic pacemaker can include pacing in an inhibited pacing mode.

Other embodiments of the invention will be apparent to those skilled in the art from consideration of the specification and practice of the invention disclosed herein. The embodiments described in detail above are exemplary only not intended to limit the spirit and scope of the invention, as defined by the following claims.

What is claimed is:

1. A method for controlling pacemaker therapy in a patient with an implanted biological pacemaker, comprising:
    pacing a heart using an electronic pacemaker;
    configuring the electronic pacemaker to periodically enter a biological pacemaker weaning mode further including the steps of:
        ceasing pacing for at least a predetermined length of time;
        monitoring the heart to detect electrical depolarizations of the heart during the predetermined length of time;
        determining the length of time between the cessation of pacing and the detected electrical depolarization;
        determining if the length of time between the cessation of pacing and the detected electrical depolarization is less than a maximum predetermined interval;
        continuing to withhold pacemaker therapy as long as the length of time is less than the maximum predetermined interval; and
        returning to a non-weaning mode if the length of time between the cessation of pacing and the detected electrical depolarization exceeds a maximum value, wherein the weaning mode further includes continuing to monitor subsequent electrical depolarizations while withholding pacing therapy;
    determining if a cardiac cycle length decreases subsequent to cessation of pacing;
    continuing to withhold pacing therapy if the cardiac cycle length decreases during the time between the cessation of pacing and the detected electrical depolarization within a predetermined number of cardiac cycles; and
    resuming pacing therapy if the cardiac cycle length does not decrease to a time less than a predetermined cycle length goal within a predetermined number of cardiac cycles.

2. The method according to claim 1, wherein the predetermined number of cardiac cycles is less than ten.

3. The method of claim 1, further including resuming pacing if the cardiac cycle length exceeds a predetermined limit.

4. The method of claim 1, further including resuming pacing by the electronic pacemaker if a patient selects electronic pacemaker stimulus on demand.

5. The method of claim 1, further including resuming pacing therapy if the cardiac cycle length exceeds a predetermined maximum cycle length.

6. A method for controlling pacemaker therapy in a patient with an implanted biological pacemaker, comprising:
    pacing a heart using an electronic pacemaker;
    ceasing pacing for at least a predetermined length of time;
    monitoring the heart to detect electrical depolarizations of the heart during the predetermined length of time; and
    determining if the electrical depolarization of the heart originated in an implanted biological pacemaker site;
    continuing to withhold pacemaker therapy if the electrical depolarization originated in the implanted biological pacemaker site and the length of time is less than the maximum predetermined interval, further including continuing to monitor subsequent electrical depolarizations while withholding pacing therapy;
    determining if a cardiac cycle length decreases subsequent to cessation of pacing;
    continuing to withhold pacing therapy if the cardiac cycle length decreases from the length of time between the cessation of pacing and the detected electrical depolarization within a predetermined number of cardiac cycles; and
    resuming pacing therapy if the cardiac cycles length does not decrease to a time less than a predetermined cycle length goal within a predetermined number of cardiac cycles.

7. The method of claim 6, further including resuming pacing therapy if the cardiac cycle length exceeds a predetermined maximum cycle length.

8. The method of claim 6, further including continuing to monitor subsequent cardiac depolarizations;
    determining a percentage of the subsequent electrical depolarizations that originate in the implanted biological pacemaker; and
    resuming pacing therapy if the percentage of subsequent electrical depolarizations originating in the implanted biological pacemaker is less than a predetermined lower limit.

9. The method of claim 8, further including providing pacing therapy in an inhibited ventricular pacing mode as long as the percentage of depolarizations originating in the implanted biological pacemaker is greater than the predetermined lower limit.

10. A method for controlling pacemaker therapy in a patient with an implanted biological pacemaker, comprising:
- pacing a heart using an electronic pacemaker;
- assessing a physiologic state of a patient;
- ceasing pacing for at least a predetermined length of time if the patient's physiologic state matches a desired predetermined state;
- monitoring the heart to detect electrical depolarizations of the heart during the predetermined length of time;
- determining if the electrical depolarization of the heart originated in an implanted biological pacemaker site;
- determining if the length of time between the cessation of pacing and the detected electrical depolarization is less than a maximum predetermined interval; and
- continuing to withhold pacemaker therapy if the electrical depolarization originated in the implanted biological pacemaker site and the length of time is less than the maximum predetermined interval; and
- continuing to monitor subsequent electrical depolarizations while withholding pacing therapy;
- determining if a cardiac cycle length decreases subsequent to cessation of pacing;
- continuing to withhold pacing therapy if the cardiac cycle length decreases from the length of time between the cessation of pacing and the detected electrical depolarization within a predetermined number of cardiac cycles; and
- resuming pacing therapy if the cardiac cycles length does not decrease to a time less than a predetermined cycle length goal within a predetermined number of cardiac cycles.

11. The method of claim 10, further including continuing to monitor subsequent cardiac depolarizations;
- determining a percentage of the subsequent electrical depolarizations that originate in the implanted biological pacemaker; and
- resuming pacing therapy if the percentage of subsequent electrical depolarizations originating in the implanted biological pacemaker is less than a predetermined lower limit.

12. The method of claim 11 further including providing pacing therapy in an inhibited ventricular pacing mode as long as the percentage of depolarizations originating in the implanted biological pacemaker is greater than the predetermined lower limit.

13. The method of claim 10, wherein the physiologic state is a resting state or a sleeping state.

14. A pacemaker system for use in patients with an implanted biological pacemaker, comprising:
- a pulse generator configured to generate electrical energy for stimulating a heart;
- at least one electrode configured to provide electrical stimulation to an atria or a ventricle of a heart and in electrical communication with the pulse generator;
- a least one sensor configured to detect electrical depolarizations of a ventricle of the heart; and
- a pacemaker processor configured to control pacing therapy according to at least one predetermined pacing mode and to enter a biological pacemaker weaning mode periodically, wherein the pacemaker is configured to cease pacing therapy for a predetermined length of time, to receive a signal from the at least one sensor indicating a depolarization of a ventricle of the heart after cessation of pacing, to determine the length of time between the cessation of pacing and the detected electrical depolarization, to determine if the length of time between the cessation of pacing and the detected electrical depolarization is less than a maximum predetermined interval, to continue to withhold pacemaker therapy as long as the length of time is less than the maximum predetermined interval, and to exit the pacemaker weaning mode if the length of time is greater than a maximum predetermined interval;
- wherein while in the pacemaker weaning mode the processor is further configured to:
- continue to monitor subsequent electrical depolarizations while withholding pacing therapy;
- determine if a cardiac cycle length decreases subsequent to cessation of pacing;
- continue to withhold pacing therapy if the cardiac cycle length decreases from the length of time between the cessation of pacing and the detected electrical depolarization within a predetermined number of cardiac cycles; and
- exit the pacemaker weaning mode if the cardiac cycles length does not decrease to a time less than a predetermined cycle length goal within a predetermined number of cardiac cycles.

15. The system of claim 14, wherein the processor is further configured to resume pacing if the cardiac cycle length exceeds a predetermined limit.

16. The system of claim 14, wherein the processor is further configured to continue to monitor subsequent cardiac depolarizations;
- determine a percentage of the subsequent electrical depolarizations that originate in the implanted biological pacemaker; and
- resume pacing therapy if the percentage of subsequent electrical depolarizations originating in the implanted biological pacemaker is less than a predetermined lower limit.

17. The system of claim 16, wherein the pacemaker is further configured to provide pacing therapy in an inhibited ventricular pacing mode as long as the percentage of depolarizations originating in the implanted biological pacemaker is greater than the predetermined lower limit.

18. The system of claim 14, further including at least one sensor configured to provide information related to a physiologic state of a patient.

19. The system of claim 18, wherein the physiologic state is a resting state or a sleeping state.

20. The system of claim 14, further including an external monitoring unit, wherein the processor is configured to withhold pacing therapy to allow pacing by the implanted biological pacemaker only when a patient is in proximity to the external monitoring unit.

* * * * *